US006884073B2

(12) United States Patent
Chilibeck (10) Patent No.: US 6,884,073 B2
(45) Date of Patent: Apr. 26, 2005

(54) TEMPORARY AND SEMI-PERMANENT DENTAL CROWNS

(76) Inventor: Richard H. Chilibeck, 5549 Forest Hill Road, Victoria, British Columbia (CA), V9E 2A8

( * ) Notice: Subject to any disclaimer, the term of this patent is extended or adjusted under 35 U.S.C. 154(b) by 247 days.

(21) Appl. No.: 10/190,827

(22) Filed: Jul. 9, 2002

(65) Prior Publication Data

US 2003/0203339 A1 Oct. 30, 2003

Related U.S. Application Data

(60) Provisional application No. 60/376,210, filed on Apr. 30, 2002.

(51) Int. Cl.[7] .............................................. A61C 5/08
(52) U.S. Cl. ...................................... 433/219; 433/218
(58) Field of Search ................................ 433/218, 219, 433/222.1, 223

(56) References Cited

U.S. PATENT DOCUMENTS

| | | | |
|---|---|---|---|
| 4,015,332 A | | 4/1977 | Manne |
| 4,678,435 A | | 7/1987 | Long |
| 5,332,390 A | * | 7/1994 | Rosellini ...................... 433/34 |
| 5,458,489 A | * | 10/1995 | Tennyson ................... 433/181 |
| 5,667,384 A | | 9/1997 | Sutter et al. |
| 5,759,032 A | | 6/1998 | Bartel |
| 5,775,913 A | * | 7/1998 | Updyke et al. ............. 433/223 |
| 5,975,906 A | | 11/1999 | Knutson |
| 5,977,199 A | | 11/1999 | Xie |
| 6,068,481 A | | 5/2000 | Worthington |
| 6,114,408 A | | 9/2000 | Dickens |
| 6,257,892 B1 | | 7/2001 | Worthington |
| 6,282,013 B1 | | 8/2001 | Ostler et al. |
| 6,299,449 B1 | | 10/2001 | Carlson |
| 2001/0036618 A1 | * | 11/2001 | Worthington ............... 433/183 |
| 2002/0025993 A1 | | 2/2002 | Klee et al. |

FOREIGN PATENT DOCUMENTS

| | | |
|---|---|---|
| CA | 2305181 | 5/1999 |
| WO | WO 95/35071 | 12/1995 |

OTHER PUBLICATIONS

Jones, Dental Cements: An Update, Journal of the Canadian Dental Association (on–line format), Sep. 1998, vol 64, Issue 8, Canadian Dental Association, Canada. http://www.cda–adc.ca/jcda/vol.–64/issue–8/569.html.

(Continued)

Primary Examiner—Cary E. O'Connor
(74) Attorney, Agent, or Firm—Paul Smith Intellectual Property Law; Paul Smith (57) ABSTRACT

A temporary crown, and variants thereof, including temporary bite caps and temporary facings, comprised of a shaped provisional (crown forms, onlays, veneers and variants thereof) and a resin filler; and a kit of provisionals, resin and auxiliary materials. The provisional has at least a partial bite layer that is integral with two opposing neighbor walls, a lingual wall and a buccal wall which, together, define a cavity to accept a tooth stub, the resin filler and optionally, a temporary adhesive. The resin filler is initially plastic and fills a void between the provisional and the tooth stub. The provisional and resin filler are selected for compatibility and cooperative curability such that following a suitable curing step, the inner layer of the provisional and the resin filler are substantially bound to and integral with one another. The provisional may have apertures through the bite layer and slits through the neighbor walls. The apertures are located in the vicinity of the cusp tips in temporaries for molars and bicuspids and in the vicinity of the junction of the lingual and incisal planes on the lingual surface in temporaries for canines and incisors. A temporary bridge can be formed in situ from a plurality of temporaries.

16 Claims, 7 Drawing Sheets

OTHER PUBLICATIONS

Way Too Cool! REVOTEK™ LC Light–cured Composite Resin for Temporary Restorations, brochure, 2001, GC America Inc., Alsip, IL, USA. http://www.geamerica.com/gcrevotk.html.

Temporary Anterior Crowns Simplified, brochure, 2001, DirectCrown LLC, Eugene, OR, USA. http://www.directcrown.com.

DirectCrown™ Crown & Bridge Materials, on–line product description, 2001, DirectCrown LLC, Eugene, OR, USA. http://www.directcrown.com/html/materials_questions.html.

Materials Science & Engineering Laboratory, Dental and Medical Materials Program, web page, 1996, National Institute of Standards and Technology, USA. www.msel.nist.gov/structure/polymers/techactav95/dentmed.html.

Materials Science & Engineering Laboratory Polymers Division, Dental and Medical Materials, Annual Report: Technical Activities 1997, National Institute of Standards and Technology, USA. http://polymers.msel.nist.gov/annuals/1997/damm.html.

* cited by examiner

Reference sign 80 added

TEMPORARY AND SEMI-PERMANENT DENTAL CROWNS

This application claims the benefit of Provisional application Ser. No. 60/376,210, filed Apr. 30, 2002.

BACKGROUND OF THE INVENTION

Permanent crowns, permanent facings and permanent bite caps have been used for many years to replace damaged or decayed teeth. They are also used to improve the aesthetics of teeth, even in cases where there is no damage or decay. The restorative process involves a number of steps. During the restorative process, a dentist must remove the damaged or decayed portion of the tooth, protect the remaining portion of the natural tooth (in the most severe case, a tooth stub) with a temporary (a "temporary" being one of a temporary crown, temporary facing or temporary bite cap) and then later, after a permanent crown, facing or bite cap has been made, restore the tooth by applying the permanent structure to the remaining portion of the natural tooth.

For the purposes of this specification, the remaining portion of the natural tooth will be referred to as the tooth when the temporization process involves an onlay or a veneer and when the temporization process involves a crown form, the remaining portion of the natural tooth will be referred to as a tooth stub. For the purposes of this specification, a "temporary bite cap" and a "temporary facing" are temporaries that cover less of the tooth than does a temporary crown. A temporary bite cap covers at least one cusp of the tooth and a temporary facing covers at least one side of a tooth. A "temporary", therefore, refers collectively to temporary crowns, and variants thereof, including temporary bite caps and temporary facings. A "provisional" refers collectively to crown forms, onlays, veneers and variants thereof. Temporaries, therefore, are further defined as the combination of a provisional, a resin filler and an optional temporary or permanent adhesive.

When a permanent crown is required, the temporization process involves fitting a temporary crown over the tooth stub, affixing the temporary crown, and then at a later time, removing the temporary crown in order to place the permanent crown on the stub. The temporary crown protects the stub and functions, with the stub, as a complete tooth while the permanent crown is being made.

When a permanent facing or a permanent bite cap is required, the temporization process involves fitting the tooth with a temporary facing or a temporary bite cap, affixing these temporaries, and then, as above, removing the temporary structure in order to place the permanent structure on the tooth.

Whether the dentist decides to use a crown form, a veneer or an onlay in the temporization process depends on the extent of damage to the tooth. When a large amount of tooth has been damaged, the tooth will be reduced to a stub and a crown form will be required. If the damage is restricted to the occlusal surface of the tooth, an onlay will be required, and if the damage has been restricted to the side of the tooth, a veneer will be required. As would be apparent, there is a broad range in the amount of tooth that is removed from case to case, and correspondingly, there is a broad range of tooth coverage provided by the various temporaries.

Having regard to the foregoing, there is no clear conceptual distinction between the various temporaries, a large veneer being essentially the same as a small crown form (for example, a ¾ crown form), and similarly, a large onlay being essentially the same as a small crown form (for example a ¾ crown form). For example, an onlay may comprise as little as one cusp and one wall and as much as the entire occlusal surface and up to ¾ of each wall. Once the temporization is comprised of more than ¾ of the walls, it is no longer considered to be an onlay, but rather, it is often referred to as a ¾ crown form. Similarly, a veneer may comprise as little as one wall. Once the temporary comprises the incisal or occlusal surface and, for example, the lingual wall and enough of the neighbour walls to extend past the narrowest part of the space between the temporary and the adjacent structure, it is usually referred to as a ¾ crown form. As would be apparent, the relationship between crown forms and veneers and onlays extends to the resultant temporary crowns, facings and bite caps.

Crown forms are used extensively in the temporization process. Until recently, these forms are typically made of stainless steel, aluminum, anodized gold, polycarbonate or clear plastic such as 3M™ clear strip forms. Many different sizes and shapes are required. For example, crown forms are sized for deciduous and permanent teeth, bicuspids, molars, canines and incisors. Accordingly, a dentist must have a large collection of crown forms readily available when doing restorative work.

In contemporary dental practice, the crown form is filled with resin and the resin is affixed non-permanently to the stub of the tooth by means of a cement, or by photo-active temporary adhesives. The resins are commonly heterogeneous materials having three essential phases: (1) a polymeric matrix which comprises the continuous phase; (2) fillers of various types, sizes, shapes and morphologies that constitute the disperse phase; and (3) an interfacial phase that, in varying degrees, bonds the continuous and disperse phases into a unitary material rather than a simple admixture It is the crown form in combination with the resin and cement that constitutes the temporary crown known previously.

The resins with which the crown form is filled typically contain predominately methacrylates, diacrylates or dimethacrylates as the polymeric matrix, as disclosed for example in U.S. Pat. No. 6,114,408, herein incorporated by reference, and additionally have a photochemical initiator, such as camphorquinone, that is either mixed with the polymorphic matrix just prior to use, or is provided in a photo-active temporary adhesive formulation. Once the temporary adhesive, resin and crown form are placed on the tooth stub, ultraviolet or visible light is used to activate the initiator, which then produces free radicals. These free radicals in turn initiate polymerization. The polymerization process is exothermic, and therefore can be irritating to the patient unless great care is taken.

For the purposed of this specification, resin filler and provisional materials that can cross-polymerize with one another, such as those listed above, or can otherwise suitably bond together, are considered to be compatible. If this polymerization can be initiated at the same time in the provisional and the resin filler, or alternatively, initiated in one and the free radicals arising therefrom then initiating polymerization in the other, then the resin filler and the provisional are considered to be cooperatively curable.

Many of the cements and temporary adhesives commonly used in the temporization process do not chemically adhere to the tooth stub, nor do they chemically adhere to the crown form. Rather, the crown form is retained on the resin and cement or temporary adhesive by physical means (at least friction and/or surface adhesion, and preferably interference) and similarly, the resin and cement or temporary adhesive are retained on the stub by physical means (friction and surface adhesion).

On the other hand, the temporary adhesives that make use of polyacrylic acid, such as zinc polycarboxylate and glass polyalkenoate (glass ionomer), provide a carboxylate group that chemically adheres to the dentin of the tooth stub (see for example the information on this subject that is recorded in http://www.cda-adc.ca/jcda/vol-64/issue-8/569.html, herein incorporated by reference). However, these temporary adhesives do not adhere to the crown form. Hence, the crown form is again held in place by physical rather than chemical means.

The crown form has to be fitted carefully in the patient's mouth as there is little room for adjustment after the temporary crown is affixed. This care is in part required because perforce the temporary crown is not firmly attached to the stub (the dentist must be able to remove it before placing the permanent crown on the stub), and, therefore, can be easily dislodged. Further, the crown form material is thin, and hence, if the temporary crown is, for example, seated proud of the other teeth, the dentist when grinding the temporary crown for bite adjustment can remove only a limited amount of material from the surface before grinding through the crown form and into the resin. Grinding through the crown form can result in distortion of the crown form, and in the worst-case scenario, failure of the temporary crown.

Recently, sculptable composite resins have been developed to overcome many of the deficiencies in the prior temporary crown technology. Products such as that sold under REVOTEK LC™ as described, for example, in http://www.gcamerica.com/gcreveotk.htlm, herein incorporated by reference, are comprised of urethane dimethylacrylate, a color filler and a photochemical initiator, and are typically provided in the form of a putty. Once the tooth stub is prepared, the putty is used to sculpt a temporary crown in situ, photo-cured briefly to stabilize the shape, and removed from the patient's mouth for final curing. The sculpted temporary crown is then affixed to the patient's tooth stub using cement or photo-active temporary adhesives. In this procedure, no crown form is used.

While the sculptable temporary crown technology improves upon the prior art, it still requires that the patient spend considerable time in the dentist's chair during the temporization process. Further, it is essential to use the services of a highly skilled technician to sculpt the temporary crown in situ.

SUMMARY OF THE INVENTION

It is an objective of the invention to provide a temporary crown of the type comprising a crown form and a resin filler (and, optionally, when the temporary crown is affixed to the tooth stub, a temporary adhesive to keep it in place). The crown form has a bite layer that is integral with two neighbour walls, a lingual wall and a buccal wall to define a cavity. The cavity accepts a tooth stub. The walls have a gingival margin distal to the bite layer.

Another objective of the invention is to provide a temporary crown that is easy to install, with a minimum of fussing over size selection. Once installed, the temporary crown should have superior retention capabilities.

In an embodiment of the invention, the crown form and the resin filler are comprised of compounds that can polymerize with one another. An inner surface of the crown form has integral therewith an incompletely polymerized layer such as occurs when polymerization is done in the presence of oxygen. This incompletely polymerized layer polymerizes with the resin filler as the resin filler is being polymerized. Thus, the crown form and the resin filler are chemically bonded to one another, such that, within the constraints of the technique, there are little or no spaces between the resin filler and the crown form.

Preferably, the crown form in a preferred embodiment of the invention is light-transmissible and more preferably it is transparent. A transparent temporary crown provides two advantages. First, air bubbles trapped within the crown form can be seen, allowing the dentist an opportunity to remove them. Removal of air bubbles increases the strength of the bond between the resin filler and the crown form. A second advantage is that the dentist is able to color-match the resin filler or the color dye with the patient's tooth color, rather than having to match the crown form with the tooth color. This reduces the number of crown forms that the dentist is required to keep on hand.

In order to achieve the foregoing objectives of the invention, the essential components of the temporary crown, namely the crown form and the resin filler, are prepared from at least one of methacrylate, diacrylate, dimethacrylate and urethane methacrylate.

More preferably, the crown form and the resin filler are comprised of 2,2'-bis [4-(2-hydroxy-3-methacryloyloxypropoxy] phenyl propane (bis-GMA) (an addition product of methylacrylic acid and bisphenol A-diglycidyl ether).

The crown form and resin filler are able to polymerize with one another. This ensures that there is good bonding between the resin filler and the crown form. The advantage of good bonding is twofold. First, the crown form is unlikely to be dislodged. Second, unlike metal crown forms, the crown form of the present invention is unlikely to be deformed, even if it is ground during the fitting process.

Preferably, both the crown form and the resin filler contain a photochemical initiator. This allows the polymerization to be done in situ, simply by shining a light source on the temporary crown.

In a preferred embodiment of the invention, the crown form is comprised of REVOTEK LC™ or Triad™.

The crown form is optionally provided with at least one aperture in the bite layer of the crown form. In crown forms for molars and bicuspids, the aperture is preferably located on the cusp tips. In crown forms for canines and incisors, the apertures are preferably located on a lingual surface in the vicinity of a junction of the lingual, incisal and neighbour planes. In this manner, the apertures function as vents for expulsion of air during fitting of the temporary crown. Expulsion of air ensures that there is good contact between the crown form and the resin filler and ensures that the product is aesthetically pleasing. The apertures should be sized to permit ready escape of gas but small enough that outflow of resin filler is inhibited.

Another optional but preferred structural feature is the presence of invaginations that define slits on the neighbour walls which extend orthogonally from the gingival margin towards the occlusal surface. During the temporization process, resin filler is extruded from the cavity through the slits in situ in order to fill the space between the temporary crown and the adjacent structure, such as a tooth or a permanent crown. This reduces the risk of food becoming lodged in the space between the temporary crown and adjacent structures.

Another objective of the invention is to provide semi-permanent crowns for children.

A preferred embodiment of the temporary crown can be used as a semi-permanent crown simply by conditioning, priming and bonding the tooth stub, then utilizing a permanent luting cement to affix the resin filler in the semi-permanent crown to the tooth stub.

Yet another objective of the invention is to provide a veneer. In order to achieve this objective, as little as one of the lingual, buccal or neighbour walls of a crown form is wholly or partly removed from the crown form and as much as substantially all of the bite layer, all of any one wall and substantially all of any other two walls that are in opposition are removed from the crown form; alternatively, a veneer structure of this sort can be created without initial inclusion of any unwanted wall or wall portion. This veneer, when used with resin filler, and optionally, temporary adhesive, forms a temporary facing.

Yet another objective of the invention is to provide an onlay. In order to achieve this objective, the buccal, lingual and neighbour walls are partly removed from the crown form; alternatively, a structure of this sort can be created without initial inclusion of any unwanted walls or wall portions. The remaining bite layer is used with resin filler, and, optionally, temporary adhesive, and is formed to the desired shape to produce a temporary bite cap.

Yet another objective of the invention is to provide kits for the temporization process. In an embodiment of the invention, the kits contain a selection of crown forms, a resin filler, a temporary adhesive, colored dyes and a shaping instrument. Kits for temporary bridges additionally contain a variety of coupling means. Kits for semi-permanent crowns additionally contain a permanent luting cement. Kits for temporary facings comprise a selection of veneers, a resin filler, a temporary adhesive, colored dyes and a shaping instrument. Similarly, kits for temporary bite caps contain a selection of onlays, a resin filler, a temporary adhesive, colored dyes and a shaping instrument.

Yet another objective of the invention is to provide a means to prepare a temporary bridge in situ, utilizing a plurality of interconnected temporary crowns. Two or more temporary crowns as described above can be used to prepare a temporary bridge in situ by coupling a series of such temporary crowns together, neighbour side to neighbour side, and encasing a coupling means such as a carbon fiber, a carbon fiber rod, a porcelain composite rod or a woven fiber material such as Ribbond-THM™ in the resin filler.

DETAILED DESCRIPTION OF PREFERRED EMBODIMENTS

Figures 1, 2:
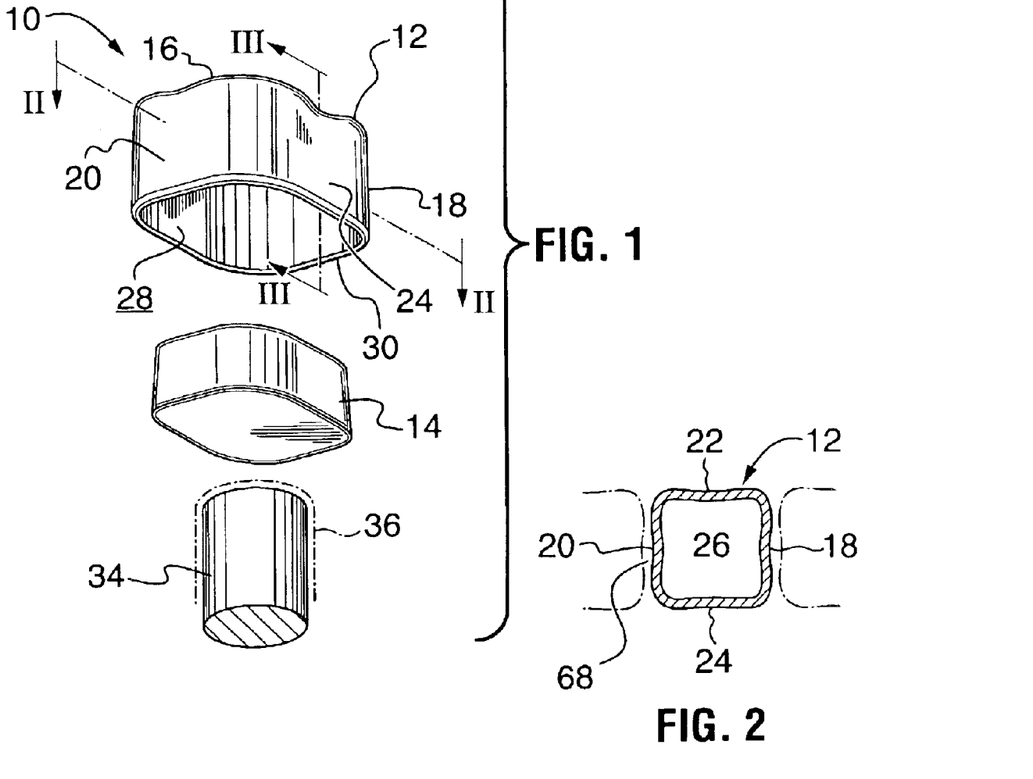
FIG. 1 is an exploded perspective view of a preferred embodiment of a temporary crown in accordance with the invention, showing a crown form, resin filler and temporary adhesive for a molar on a tooth stub.
FIG. 2 is a cross section of the crown form shown as part of the temporary crown in FIG. 1 taken along the line II—II of FIG. 1.

A temporary crown, generally indicated by the reference number 10, has a crown form 12 and a resin filler 14 (FIG. 1 and 2). The crown form 12 has a bite layer 16 that is integral with two neighbour walls 18, 20, a lingual wall 22 and a buccal wall 24 to define a cavity 26. The walls 18, 20, 22 and 24 have a gingival margin 30 distal to the bite layer 16. The cavity 26 accepts a tooth stub 34 and the resin filler 14 fills a void (not shown) between an inner surface 28 of the crown form 12 and the tooth stub 34. A temporary adhesive 36 is optionally applied to the crown form 12. Additionally, a color dye (not shown) is optionally applied to the inner surface 28 of the crown form 12 in order to color the temporary crown 10.

Figure 3:
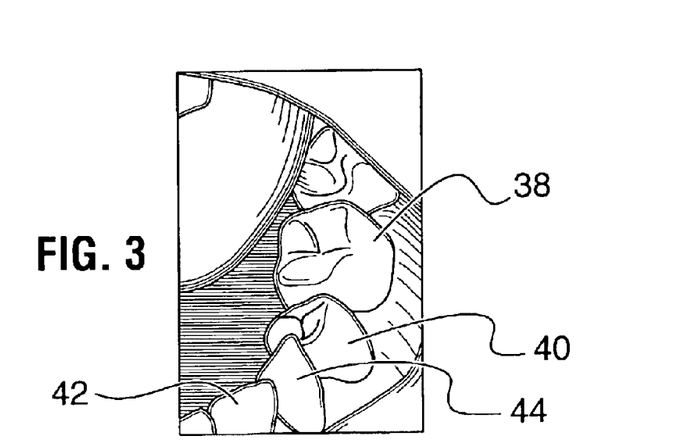
FIG. 3 is a perspective view of a representative patient's mouth, showing an incisor, a canine, a bicuspid and a molar.

There can be a number of different types of temporary crowns 10, depending whether a molar 38, a bicuspid 40, an incisor 42 or a canine 44 is to be crowned (FIG. 3). Further, there are different shapes and sizes of temporary crowns 10, ranging in size from one that would fit a deciduous tooth (not shown) to one that would fit a permanent tooth (not shown). Accordingly, a kit for temporary crowns 10 contains a selection of crown forms 12, in addition to resin filler 14, a shaping instrument (not shown) and optionally, temporary adhesive 36 and color dyes (not shown).

Figure 4:
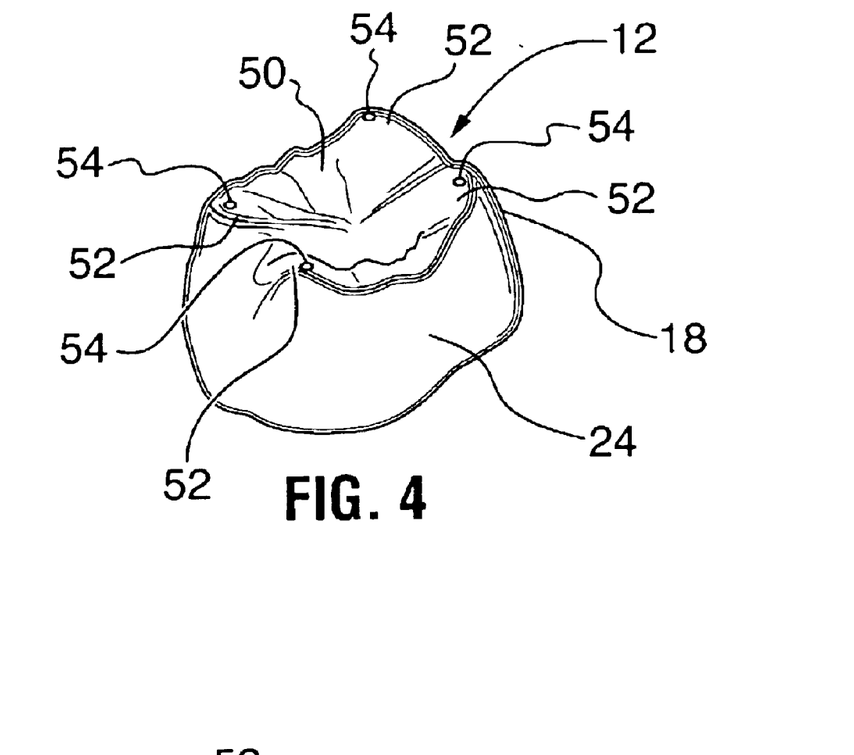
FIG. 4 is a perspective view of a preferred embodiment of a crown form according to the invention, suitable for a molar.
Figure 5:
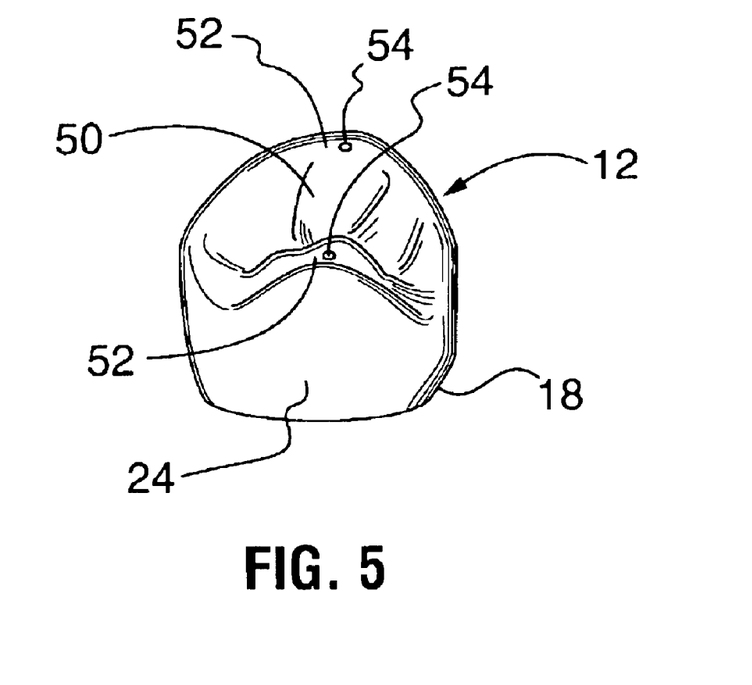
FIG. 5 is a perspective view of a preferred embodiment of a crown form according to the invention, suitable for a bicuspid.

The crown form 12 for a molar 38 has a bite layer 16 with an occlusal surface 50. The occlusal surface 50 has cusp tips 52 that correspond to the cusp tips 52 of the molar 38 (FIG. 4). Similarly, the crown form 12 for a bicuspid 40 has a bite layer 16 with an occlusal surface 50 (FIG. 5). The occlusal surface 50 has cusp tips 52 that correspond to the cusp tips 52 of the bicuspid 40. Both crown forms 12 have apertures 54 located on the cusp tips 52. There are preferably three apertures 54 in crown forms 12 for maxillary molars 38, four apertures 54 in crown forms 12 for mandibular molars 38 and two apertures 54 in crown forms for the bicuspids 40. These apertures 54 function as vents to permit the expulsion of air and prevent the extrusion of resin filler 14 from the temporary crown 10 during fitting of the temporary crown 10. This improves the appearance of the temporary crown 10, as air bubbles are forced out of the unpolymerized, and hence plastic resin filler 14 by exerting pressure on the crown form 12 during fitting. The apertures 54 should be large enough for effective venting but small enough that there is little tendency for the resin filler to flow from inside the temporary crown outwards through the apertures 54.

Figure 6:
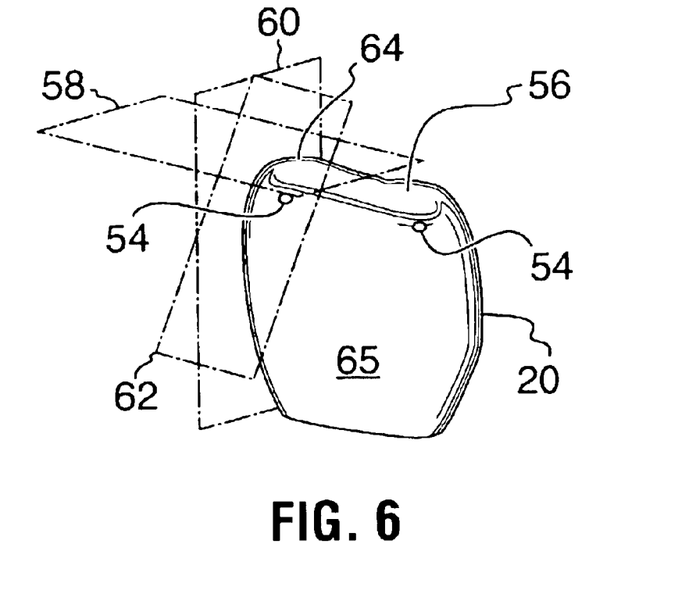
FIG. 6 is a perspective view of a preferred embodiment of a crown form according to the invention, suitable for an incisor.

The crown form 12 for an incisor 42 has a bite layer 16 with an incisal edge 56 that correspond to the incisal edge 56 of the teeth (FIG. 6). In order to locate the apertures 54, lines are drawn to define an incisal plane 58, a neighbour plane 60 and a lingual plane 62. The incisal 58 and lingual planes 62 intersect to form a junction of the incisal and lingual planes 64 on a lingual surface 65 proximal to their intersection with the neighbour plane 60 and it is in this vicinity that the apertures 54 are located. There are preferably two apertures 54 in the crown forms 12 for the incisors 42. The apertures 54 function as above.

Figure 7:
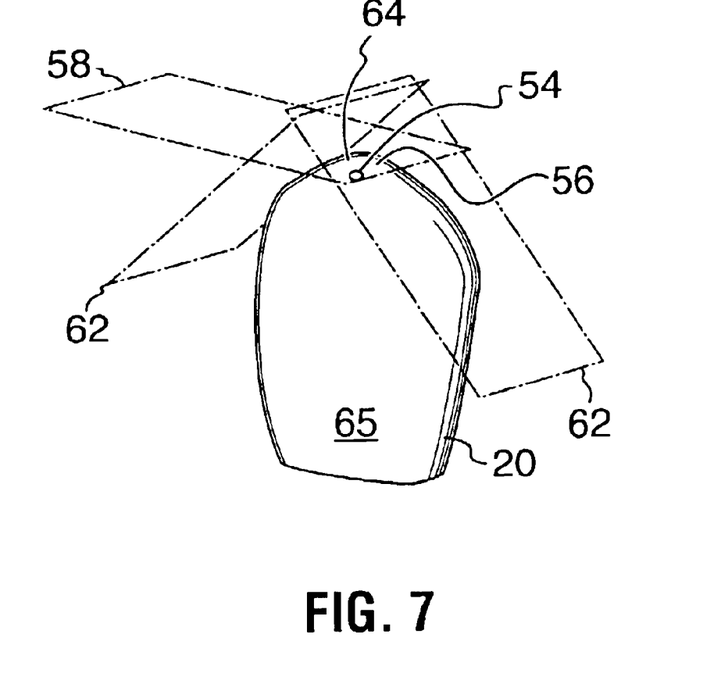
FIG. 7 is a perspective view of a preferred embodiment of a crown form according to the invention, suitable for a canine.

The crown form 12 for a canine 44 has a bite layer 16 with an incisal edge 56 that correspond to the incisal edge 56 of the teeth (FIG. 7). In order to locate the apertures 54, lines are drawn to define an incisal plane 58, and two lingual planes 62. These planes intersect to form a junction of the incisal and lingual planes 64 on a lingual surface 65 and it is in this vicinity that the apertures 54 are located. There is preferably one aperture 54 in the crown form 12 for the canines 44. The apertures 54 function as above.

Figure 8:
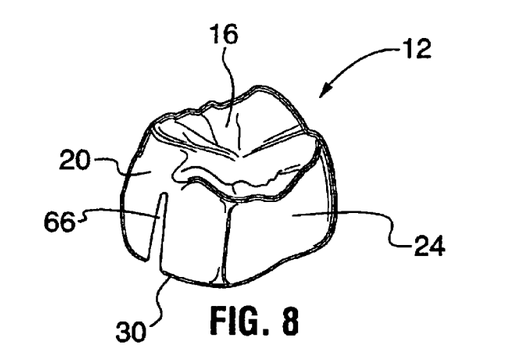
FIG. 8 is a perspective view of a preferred embodiment of a crown form according to the invention showing a slit extending from the gingival margin towards a bite layer of the crown form.
Figure 9:
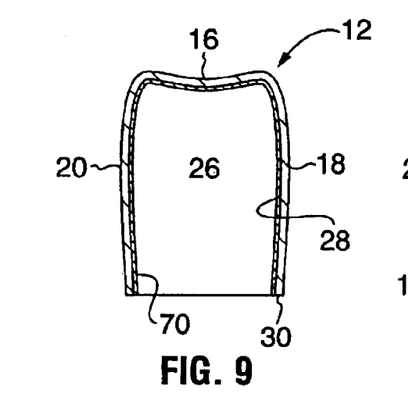
FIG. 9 is a longitudinal section of the crown form shown as part of the temporary crown in FIG. 1 taken along line III—III in FIG. 1.

Regardless of the tooth involved, preferred embodiments of the crown forms 12 have invaginations on the neighbour walls 18, 20 that define a slit 66 that originates at the gingival margin 30 and extends orthogonally towards the bite layer 16 (FIG. 8). The function of the slits 66 is to permit extrusion of the resin filler 14 from the cavity 26, through the slits 66 and into a space 68 (see FIG. 2) that is found between the temporary crown and its adjacent structures, whether they are teeth 38, 40, 42, 44 or permanent crowns 10. Filling the space 68 during fitting reduces the opportunity for food to become lodged there. The slits 66 also permit more flexibility in choosing the correct size of crown form 12. This is because the slits 66 can be expanded slightly, but more importantly, because the extruded resin filler 14 fills the space 68.

The crown form 12 is preferably comprised of at least a polymer of bis-GMA, (an addition product of methylacrylic acid and bisphenol A-diglycidyl ether) and a photochemical free radical initiator. Examples of suitable crown form materials include unfilled bis-GMA based resin, partially filled bis-GMA based resin, microfilled bis-GMA based resin, macrofilled bis-GMA based resin, and bis-GMA based resin containing glass ionomer, acrylic, methylmethacrylate or polycarbonate. Triad™ and REVOTEK LC™ are also suitable crown form materials. The resin filler 14 is capable of polymerization with the crown form 12 and is preferably comprised at least of bis-GMA, solid additives, and a photochemical free radical initiator. The solid additives provide coloration to the resin filler 14 and are, therefore, available in many shades such as those found in the Vita™ shade guide. Methacrylate, diacrylate, dimethacrylate or urethane methacrylate are also suitable crown form 12 and resin filler 14 materials.

In a preferred embodiment of the invention, the crown form 12 is transparent. This allows the dentist to view the resin filler 14 as the temporary crown 10 is being formed and to examine the temporary crown 10 for air bubbles in the resin filler 14. The use of a transparent crown form 12 also allows the dentist to choose the most suitable color of resin filler 14 for the patient. This reduces the number of crown forms 12 that the dentist is required to have on hand.

In another embodiment of the invention, the crown form 12 is comprised of putty that is polymerized ex situ and supplied as a resilient crown form 12. As an example, but not to be limiting, the crown form 12 is formed from REVOTEK LC™, Triad™, FRIT™ or Iso-Temp™.

The crown forms 12 are preferably supplied as a complete collection corresponding to deciduous and permanent teeth, and are in a variety of sizes. The crown forms 12 may be sold as part of a kit (not shown), which would include resin filler 14, temporary adhesive, color dyes and a shaping instrument (not shown).

Formation of the temporary crown 12 by a dentist involves selecting the appropriate crown form 12 with its incompletely polymerized layer 70, filling the crown form 12 with resin filler 14, fitting the crown form 12 and resin filler 14 onto the tooth stub 34, and photopolymerizing or autopolymerizing the resin filler 14 and incompletely polymerized layer 70 of the crown form 12 in situ. This results in formation of a relatively secure bond between the resin filler 14 and the crown form 12, which, within the constraints of the technique, should be void of discontinuities. The resulting temporary crown 10 is then "pluck tested". This test simply determines if the temporary crown 10 has adhered to the tooth stub 34. If plucking the temporary crown 10 dislodges it, then the crown form 12 is coated with temporary adhesive 36, the resin filler 14 and crown form 12 are placed on the tooth stub 34, and the temporary adhesive 36 is photopolymerized or autopolymerized. The use of temporary adhesive 36 however is not always necessary, as sometimes the pluck test reveals that there is sufficient attachment of the temporary crown 10 to the tooth stub 34 without the need to add any temporary cement or adhesive 36.

Figure 10:
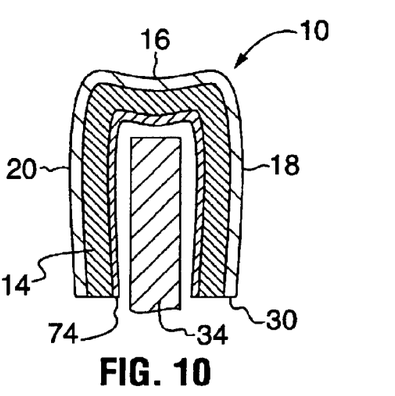
FIG. 10 is a longitudinal section of a preferred embodiment of a semi-permanent crown according to the invention showing the placement of a permanent luting cement. The line indicated by III—III in FIG. 1 shows the location of the section.

In an alternative embodiment of the invention, the temporary crown 10 is a semi-permanent crown for use on children (FIG. 10). These may be provided individually or as kits. The kits are as described above for temporary crowns 12 with the addition of a permanent luting cement 74. In semi-permanent crowns, the semi-permanent crown is as described above, with the exception of the temporary adhesive 36. In order to affix the semi-permanent crown 10 to the tooth stub 34, a permanent luting cement 74, rather than the temporary adhesive 36, is used to affix the resin filler 14 and crown form 12. The semi-permanent crown 10 can be replaced with a permanent crown when the tooth stub 34 ceases to erupt. This usually takes a number of years; years during which otherwise a child would ordinarily have a stainless steel temporary crown.

Figure 11:
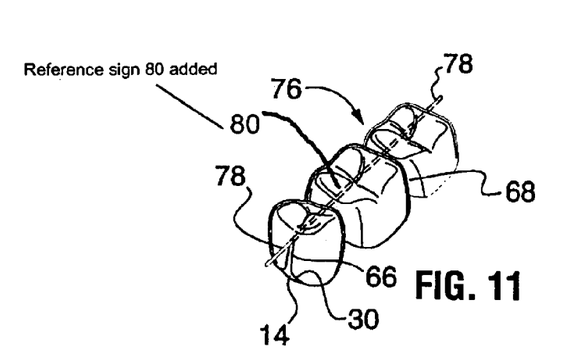
FIG. 11 is a perspective view of a preferred embodiment of a temporary bridge constructed in accordance with the invention.

In yet another embodiment of the invention, a temporary bridge 76 is formed in situ, from a plurality of temporary crowns 10 (FIG. 11). A steel wire 78 joins the temporary crowns 10 to one another along a distal-medial axis 80. The temporary bridge may alternatively be joined with a carbon fiber, a carbon fiber rod, a porcelain composite rod or Ribbond-THM™. Kits for temporary bridges 76 contain crown forms 12, resin filler 14, steel wire 78, carbon fiber, carbon fiber rod or Ribbond-THM™, a shaping instrument (not shown) and optionally temporary adhesive 36 and color dye (not shown).

The steps involved in forming the temporary bridge 76 are essentially the same as the steps taken to form an individual temporary crown 10, except that the steel wire 78 is embedded in the resin filler 14 subtending the bite layer 16 of the crown form 12 and passing through the slits 66 such that it traverses the tooth stubs 34. Resin filler 14 is extruded through the slits 66 and into the spaces 68 between the temporary crowns 10. The temporary bridge 76 is then polymerized in situ.

Figure 12:
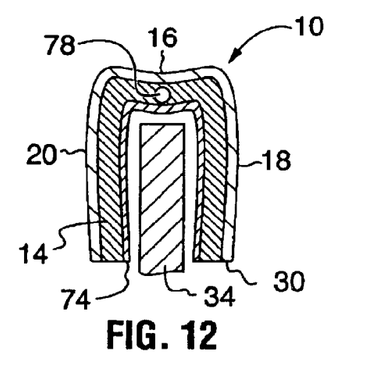
FIG. 12 is a longitudinal section of a preferred embodiment of a temporary bridge as shown in FIG. 11. The line indicated by III—III in FIG. 1 shows the location of the section.

In many tooth repair situations, the tooth does not have to be reduced to a stub; rather, a less extensive part of the tooth 38, 40, 42 44 is removed. If the damage is located on a side of the tooth 38, 40, 42, 44, a temporary facing 82 may suffice. As shown in FIG. 12, in one embodiment of the invention, the temporary facing 82 is comprised of a veneer 84 and a resin filler 14. The veneer 84 is structurally the same as a crown form 12 except that all or a portion of one of the first neighbour wall 18, the lingual wall 22 or the buccal wall 24 is first removed from a complete crown form. Thus, the veneer 84 has one of a foreshortened first neighbour wall (not shown), a foreshortened lingual wall 102 (shown by way of example in FIG. 13), or a foreshortened buccal wall (not shown).

Figure 13:
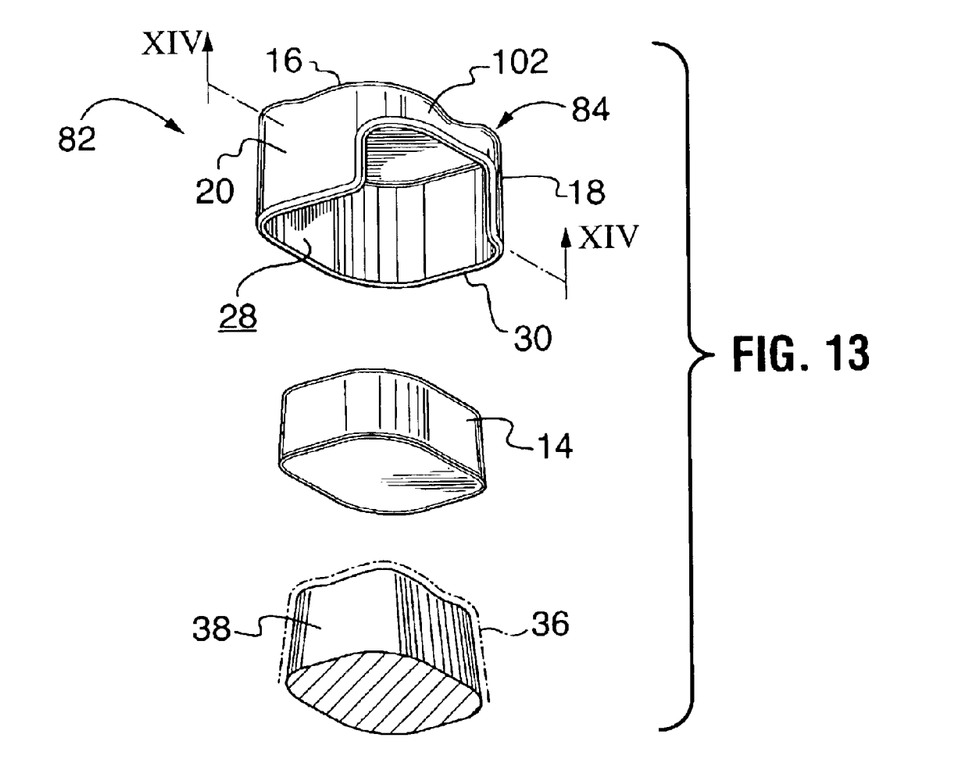
FIG. 13 is an exploded perspective view of one preferred embodiment of a temporary facing.
Figure 14:
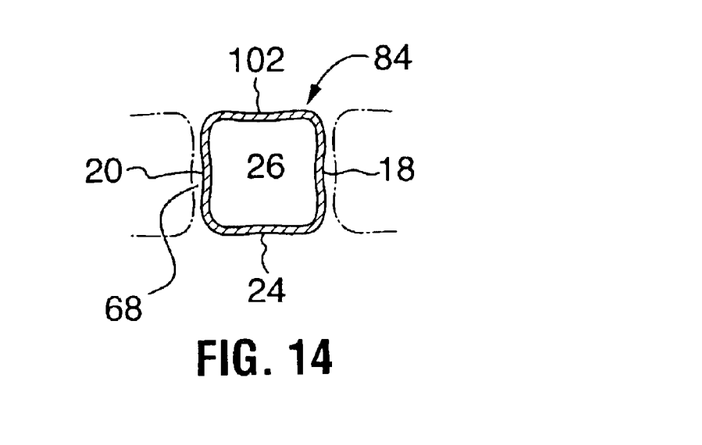
FIG. 14 is a cross section of the veneer shown as part of the temporary facing shown in FIG. 13, taken along line XIV of FIG. 13.

In the embodiment shown in FIG. 13, the veneer 84 has a bite layer 16 that is integral with a first and second neighbour wall 18, 20, a foreshortened lingual wall 102 and a buccal wall 24, to define a cavity 26. The cavity 26 permits the veneer 84 to be fitted to a tooth 38, and the resin filler 14 fills a void (not shown) between an inner surface 28 of the veneer 84 and the tooth 38. A temporary adhesive 36 is optionally applied to the tooth 38 and the temporary facing 82. Additionally, a color dye (not shown) is optionally applied to the inner surface 28 of the veneer 84 in order to color the temporary facing 82.

Figure 15:
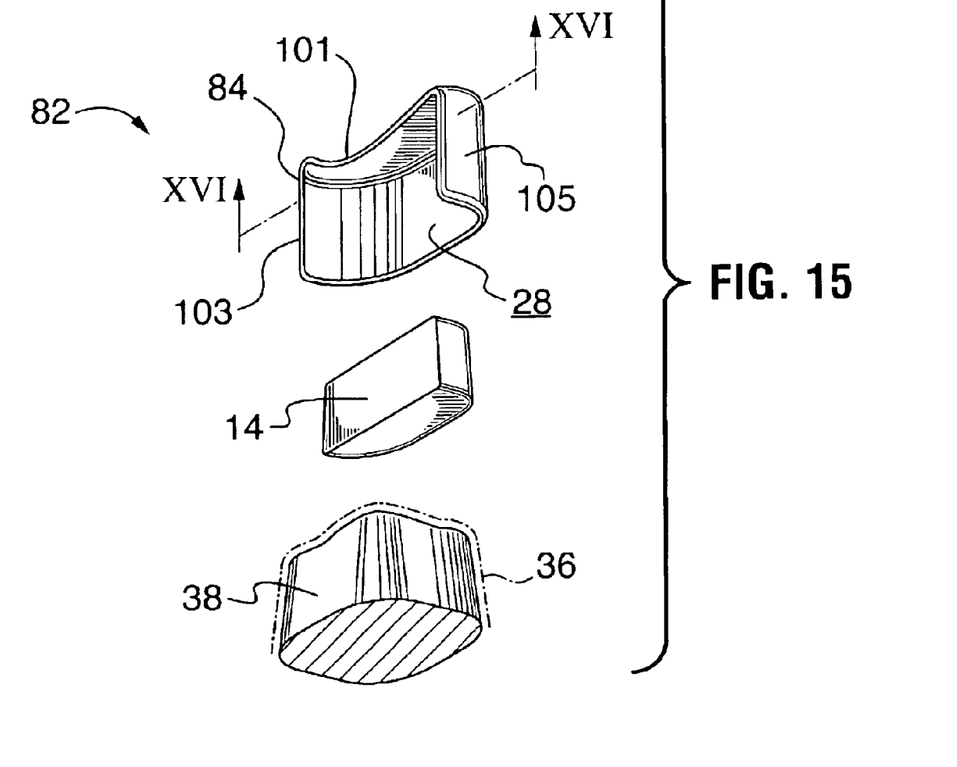
FIG. 15 is an exploded perspective view of a second preferred embodiment of a temporary facing.
Figure 16:
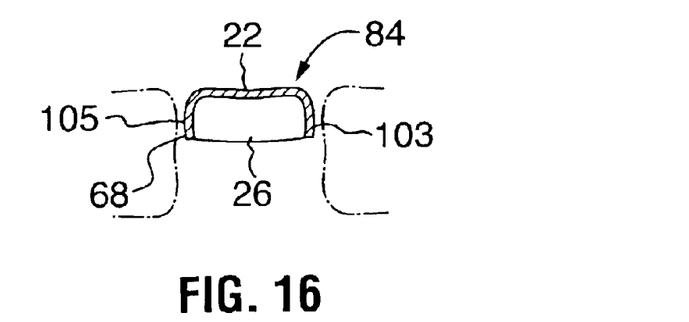
FIG. 16 is a cross section of the veneer shown as part of the temporary facing shown in FIG. 15, taken along line XVI of FIG. 15.

In the embodiment shown in FIG. 15, the veneer 84 has a much reduced bite layer 101 that is integral with the lingual wall 22 and a pair of truncated neighbour walls 103, 105. A small cavity 28 is defined by the walls 22, 103, 105 and the bite layer 101. The cavity 26 permits the veneer 84 to be fitted to a tooth 38, and the resin filler 14 fills a void (not shown) between an inner surface 28 of the veneer 84 and the tooth 38. A temporary adhesive 36 is optionally applied to the tooth 38 and the temporary facing 82. Additionally, a color dye (not shown) is optionally applied to the inner surface 28 of the veneer 84 in order to color the temporary facing 82.

The temporary facing 82 and the veneer 84 have all the chemical features of the temporary crown 10 and crown form 12, respectively, described above.

Figure 17:
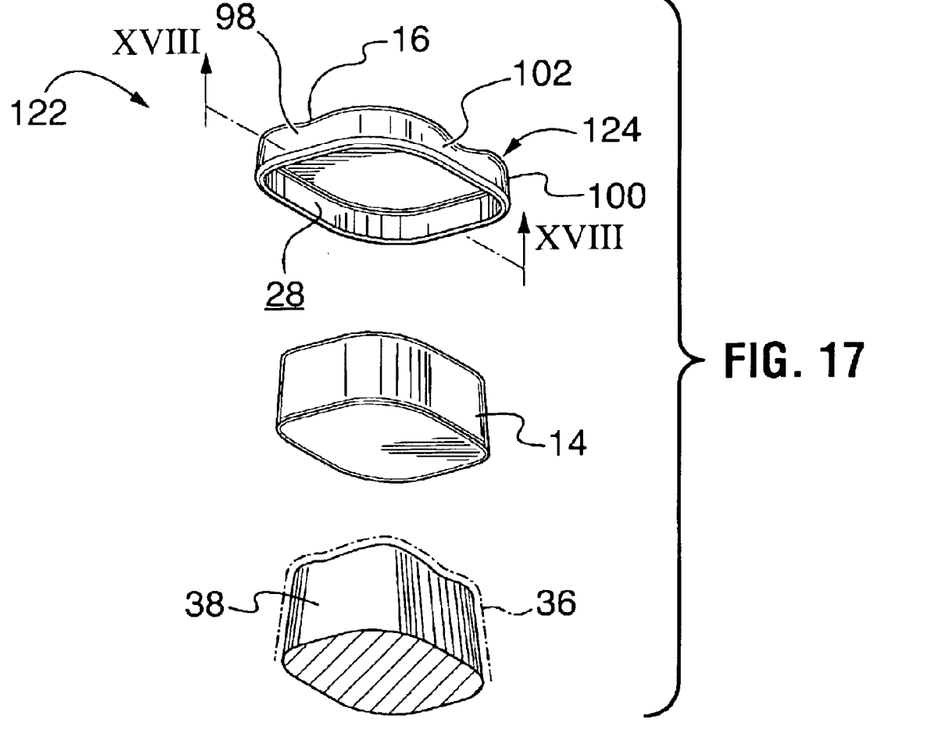
FIG. 17 is an exploded perspective view of a preferred embodiment of a temporary bite cap.
Figure 18:
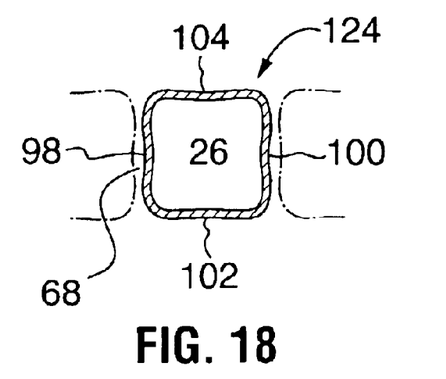
FIG. 18 is a cross section of the onlay shown as part of the temporary bite cap shown in FIG. 17, taken along line XVIII of FIG. 17.

In yet another embodiment of the invention, a temporary bite cap 122 is provided. The temporary bite cap 122 is employed when the surface of the tooth 38, 40, 42, 44 corresponding to the bite layer 16 is worn or damaged. In one embodiment of the invention, shown in FIG. 17, the temporary bite cap 122 is comprised of an onlay 124 and a resin filler 14. The onlay 124 is structurally the same as a crown form 12 except that most of the neighbour walls 18, 20, lingual wall 22 and buccal wall 24 are first removed. Thus, the onlay 124 has a bite layer 16 that is integral with foreshortened neighbour walls 98, 100, a foreshortened lingual wall 102 and a foreshortened buccal wall 104, to define a cavity 26. The cavity 26 permits the veneer 84 to be fitted to a tooth 38 and the resin filler 14 fills a void (not shown) between an inner surface 28 of the onlay 124 and the tooth 38. A temporary adhesive 36 is optionally applied to the tooth 38 and the onlay 124. Additionally, a color dye (not shown) is optionally applied to the inner surface 28 of the onlay 124 in order to color the temporary bite cap 122.

The temporary bite cap 122 and the onlay 124 have all the chemical features of the temporary crown 10 and crown form 12, respectively, described above.

The foregoing description of the temporary crown, semi-permanent crown and the temporary bridge of the present invention describes the preferred embodiments and is not meant to be limiting. As would be apparent to one skilled in the art, there can be, for example, variation in materials, number of vents, and slit angle, the number of temporary crowns used in a temporary bridge, and the lifetime of the temporary bridge. Further, the invention provides for variations in the structure of the provisionals. As would be apparent to one skilled in the art, there is a conceptual continuum that embraces onlays, veneers and crown forms and hence, the resulting temporaries, including temporary facings, bite caps and crowns. For example, an onlay may comprise as little as one cusp and one wall and as much as the entire occlusal surface and up to ¾ of each wall. Once the temporization is comprised of more than ¾ of the walls, it is no longer considered to be an onlay, but rather, it is a ¾ crown form. Similarly, a veneer may comprise as little as one wall. Once the temporary comprises the incisal or occlusal surface and, for example, the lingual wall and enough of the neighbour walls to extend past the narrowest part of the space between the temporary and the adjacent structure, it is usually referred to as a ¾ crown form.

What is claimed is:

1. A temporary for protecting a tooth stub comprised of a provisional and a resin filler, said provisional having at least a partial bite layer, a pair of opposing neighbour walls, which are at least partial walls, at least a partial lingual wall and at least a partial buccal wall, said lingual and buccal walls in opposition, said bite layer integral with the neighbour, lingual and buccal walls to define a cavity to accept the tooth stub and resin filler, the resin filler containing a selected coloring agent and being initially plastic and filling a void between the provisional and the tooth stub, the walls of the provisional being light-transmissible and at least an inner surface of the provisional and the resin filler being comprised of bis-GMA or chemicals selected from the group consisting of methacrylates, dimethacrylates and diacrylates, the composition of at least an inner surface of the provisional and the resin filler being selected for compatibility and cooperative curability, and the resin filler being initially unpolymerized and the provisional having an initially incompletely polymerized layer integral with the inner surface of the provisional, such that after polymerization of the resin filler, completion of the polymerization of the initially incompletely polymerized layer, and a suitable curing step, the provisional becomes substantially bound to and integral with the resin filler.

2. A temporary for protecting a tooth stub comprised of a provisional and a resin filler, said provisional having at least a partial bite layer, a pair of opposing neighbor walls, which are at least partial walls, at least a partial lingual wall and at least a partial buccal wall, said lingual and buccal walls in opposition, said bite layer integral with the neighbour, lingual and buccal walls to define a cavity to accept the tooth stub and resin filler, the resin filler being initially plastic and filling a void between the provisional and the tooth stub, the composition of at least an inner surface of the provisional and the resin filler being selected for compatibility and cooperative curability, at least an inner surface of the provisional and the resin filler being comprised of urethane dimethylacrylate, a color filler and a photochemical initiator, said resin filler being initially unpolymerized and wherein the provisional has an initially incompletely polymerized layer integral with the inner surface of the provisional, such that after polymerization of the resin filler and completion of the polymerization of the initially incompletely polymerized layer, and a suitable curing step, the resin filler and the provisional are comprised substantially of a polymeric matrix and the resin filler becomes substantially bound to and integral with the provisional.

3. A temporary for protecting a tooth stub comprised of a provisional and a resin filler, said provisional having at least a partial bite layer, wherein the bite layer has an incisal edge, said incisal edge being integral with the lingual wall to define at least one junction of an incisal plane and a lingual plane on a lingual surface, said lingual wall having at least one aperture located in the vicinity of the junction of the incisal and lingual nianes which during fitting is a vent for expulsion of air, a pair of opposing neighbour walls, which are at least partial walls, wherein at least one of the neighbour walls has a gingival margin distal to the bite layer and is invaginated to define a slit extending from the gingival margin towards the bite layer of said provisional, such that during fitting, resin filler is extruded through the slit into a space between the temporary and adjacent structures to provide contact between the temporary and adjacent structures, at least a partial lingual wall and at least a partial buccal wall, said lingual and buccal walls in opposition, said bite layer integral with the neighbour, lingual and buccal walls to define a cavity to accept the tooth stub and resin filler, the resin filler being initially plastic and filling a void between the provisional and the tooth stub, the composition of at least an inner surface of the provisional and the resin filler being selected for compatibility and cooperative curability and the provisional having an incompletely polymerized layer integral with an inner surface of the provisional, such that after polymerization of the resin filler and following a suitable curing step, the resin filler becomes substantially bound to and integral with the provisional.

4. A temporary to protect a tooth stub comprised of a provisional and a resin filler, said provisional being light-transmissible, said provisional having a bite layer, a pair of opposing neighbour walls, a lingual wall and a buccal wall, at least one of the neighbour walls having a gingival margin distal to the bite layer and being invaginated to define a slit extending from the gingival margin towards the bite layer of said provisional, such that during fitting, resin filler is extruded through the slit into a space between the provisional and an adjacent structure to provide contact with the adjacent structure, said lingual and buccal walls in opposition, said bite layer integral with the neighbour, lingual and buccal walls to define a cavity to accept the tooth stub and resin filler, said resin filler being unpolymerized and filling a void between the provisional and the tooth stub, said bite layer having an occlusal surface, said occlusal surface having at least one cusp tip, and said bite layer having at least one aperture in the vicinity of the cusp tip, which during fitting is a vent for expulsion of air, wherein the provisional and the resin filler are comprised of bis-GMA or chemicals selected from the group consisting of methacrylates, dimethacrylates and diacrylates and at least one photochemical free radical initiator, and the provisional having an incompletely polymerized layer integral with an inner surface of the provisional, such that after polymerization of the resin filler, the provisional is bound to the resin filler.

5. A temporary to protect a tooth stub comprised of a provisional and a resin filler, said provisional having a bite layer, a pair of opposing neighbour walls, a lingual wall and a buccal wall, at least one of the neighbour walls having a gingival margin distal to the bite layer and being invaginated to define a slit extending from the gingival margin towards the bite layer of said provisional, such that during fitting, resin filler is extruded through the slit into a space between the provisional and an adjacent structure to provide contact with the adjacent structure, said lingual and buccal walls in opposition, said bite layer integral with the neighbour, lingual and buccal walls to define a cavity to accept the tooth stub and resin filler, said resin filler being unpolymerized and filling a void between the provisional and the tooth stub, said bite layer having an occlusal surface, said occlusal surface having at least one cusp tip, and said bite layer having at least one aperture in the vicinity of the cusp tip, which during fitting is a vent for expulsion of air, wherein the provisional and the resin filler are comprised of urethane dimethylacrylate, a color filler and at least one photochemical free radical initiator, and the provisional having an incompletely polymerized layer integral with an inner surface of the provisional, such that after polymerization of the resin filler, the provisional is bound to the resin filler.

6. A temporary to protect a tooth stub comprised of a provisional and a resin filler, said provisional being light-transmissible, said provisional having a bite layer, a pair of opposing neighbour walls, a lingual wall and a buccal wall, at least one of the neighbour walls having a gingival margin distal to the bite layer and being invaginated to define a slit extending from the gingival margin towards the bite layer of said provisional, such that during fitting, resin filler is extruded through the slit into a space between the provisional and an adjacent structure to provide contact with the adjacent structure, said lingual and buccal walls in opposition, said bite layer integral with the neighbour, lingual and buccal walls to define a cavity to accept the tooth stub and resin filler, said resin filler being unpolymerized and filling a void between the provisional and the tooth stub, said bite layer having an incisal edge, said incisal edge being integral with the lingual wall to define at least one junction of an incisal plane and a lingual plane on a lingual surface, said lingual wall having at least one aperture located in the vicinity of the junction of the incisal and lingual planes which during fitting is a vent for expulsion of air, wherein the provisional and the resin filler are comprised of bis-GMA or chemicals selected from the group consisting of methacrylates, dimethacrylates and diacrylates and at least one photochemical free radical initiator, and the provisional having an incompletely polymerized layer integral with an inner surface of the provisional, such that after polymerization of the resin filler, the provisional is bound to the resin filler.

7. The temporary of claim 6, wherein at least an inner surface of the provisional and the resin filler is comprised of bis-GMA or chemicals selected from the group consisting of methacrylates, dimethacrylates and diacrylates, such that following a suitable curing step, the resin filler and the provisional are comprised substantially of a polymeric, matrix.

8. A temporary to protect a tooth stub comprised of a provisional and a resin filler, said provisional having a bite layer, a pair of opposing neighbour walls, a lingual wall and a buccal wall, at least one of the neighbour walls having a gingival margin distal to the bite layer and being invaginated to define a slit extending from the gingival margin towards the bite layer of said provisional, such that during fitting, resin filler is extruded through the slit into a space between the provisional and an adjacent structure to provide contact with the adjacent structure, said lingual and buccal walls in opposition, said bite layer integral with the neighbour, lingual and buccal walls to define a cavity to accept the tooth stub and resin filler, said resin filler being unpolymerized and filling a void between the provisional and the tooth stub, said bite layer having an incisal edge, said incisal edge being integral with the lingual wall to define at least one junction of an incisal plane and a lingual plane on a lingual surface, said lingual wall having at least one aperture located in the vicinity of the junction of the incisal and lingual planes which during fitting is a vent for expulsion of air, wherein the provisional and the resin filler are comprised of urethane dimethylacrylate, a color filler and at least one photochemical free radical initiator, and the provisional having an incompletely polymerized layer integral with an inner surface of the provisional, such that after polymerization of the resin filler, the provisional is bound to the resin filler.

9. The provisional of claim 8, wherein the inner surface of the provisional is coated with a color dye.

10. A provisional for use with a resin filler to protect a tooth stub, wherein the provisional is transparent, said provisional having a bite layer, a pair of opposing neighbour walls, at least one of the neighbour walls having a gingival margin distal to the bite layer and being invaginated to define a slit extending from the gingival margin towards the bite layer of said provisional, such that during fitting, resin filler is extruded through the slit into a space between the provisional and an adjacent structure to provide contact with the adjacent structure, a lingual wall and a buccal wall, said lingual and buccal walls in opposition, said bite layer integral with the neighbour, lingual and buccal walls to define a cavity to accept the tooth stub and resin filler, said bite layer having an occlusal surface, said occlusal surface having at least one cusp tip, and said bite layer having at least one aperture in the vicinity of the cusp tip, which during fitting is a vent for expulsion of air, wherein the provisional and the resin filler are comprised of bis-GMA or chemicals selected from the group consisting of methacrylates, dimethacrylates and diacrylates and at least one photochemical free radical initiator, and the provisional having an incompletely polymerized layer integral with an inner surface of the provisional, such that after polymerization of the resin filler, the provisional is bound to the resin filler.

11. The provisional of claim 10, wherein the inner surface of the provisional is coated with a colour dye.

12. A provisional for use with a resin filler to protect a tooth stub wherein the provisional is transparent, said provisional having a bite layer, a pair of opposing neighbour walls, at least one of the neighbour walls having a gingival margin distal to the bite layer and being invaginated to define a slit extending from the gingival margin towards the bite layer of said provisional, such that during fitting, resin filler is extruded through the slit into a space between the provisional and an adjacent structure to provide contact with the adjacent structure, a lingual wall and a buccal wall, said lingual and buccal walls in opposition, said bite layer having an incisal edge, said incisal edge being integral with the lingual wall to define at least one junction of an incisal plane and a lingual plane on a lingual surface, said lingual wall having at least one aperture located in the vicinity of the junction of the incisal and lingual planes which during fitting is a vent for expulsion of air, wherein the provisional and the resin filler are comprised of bis-GMA or chemicals selected from the group consisting of methacrylates, dimethacrylates and diacrylates and at least one photochemical free radical initiator, and the provisional having an incompletely polymerized layer integral with an inner surface of the provisional, such that after polymerization of the resin filler, the provisional is bound to the resin filler.

13. A provisional for use with a resin filler to protect a tooth stub, said provisional having a bite layer, a pair of opposing neighbour walls, at least one of the neighbour walls having a gingival margin distal to the bite layer and being invaginated to define a slit extending from the gingival margin towards the bite layer of said provisional, such that during fitting, resin filler is extruded through the slit into a space between the provisional and an adjacent structure to provide contact with the adjacent structure, a lingual wall and a buccal wall, said lingual and buccal walls in opposition, said bite layer integral with the neighbour, lingual and buccal walls to define a cavity to accept the tooth stub and resin filler, said bite layer having an occlusal surface, said occlusal surface having at least one cusp tip, and said bite layer having at least one aperture in the vicinity of the cusp tip, which during fitting is a vent for expulsion of air, wherein the provisional is comprised of urethane dimethylacrylate, a color filler at least one photochemical free radical initiator, and the provisional having an incompletely polymerized layer integral with an inner surface of the provisional, such that after polymerization of the resin filler, the provisional is bound to the resin filler.

14. A provisional for use with a resin filler to protect a tooth stub wherein the provisional is light-transmissible, said provisional having a bite layer, a pair of opposing neighbour walls, a lingual wall and a buccal wall, said lingual and buccal walls in opposition, said bite layer integral with the neighbour, lingual and buccal walls to define a cavity to accept the tooth stub and resin filler, said bite layer having an incisal edge, said incisal edge being integral with the lingual wall to define at least one junction of an incisal plane and a lingual plane on a lingual surface, said lingual wall having at least one aperture located in the vicinity of the junction of the incisal and lingual planes which during fitting is a vent for expulsion of air, wherein the provisional is comprised of urethane dimethylacrylate, a color filler and at least one photochemical free radical initiator, and the provisional having an incompletely polymerized layer integral with an inner surface of the provisional, such that after polymerization of the resin filler, the provisional is bound to the resin filler.

15. A temporary bridge to protect a plurality of tooth stubs comprised of a plurality of temporaries and a coupling means, each temporary comprised of a provisional and a resin filler, said resin filler being unpolymerized and filling a void between the provisional and the tooth stub, said provisional having a bite layer, a pair of opposing neghbour walls, a lingual wall and a buccal wall, said lingual and buccal walls in opposition, said bite layer integral with the neighbour, lingual and buccal walls to define a cavity to accept the tooth stub and resin filler, said neighbour, buccal and lingual walls having a gingival margin distal to the bite layer, wherein the neighbour walls are invaginated to define a slit extending from the gingival margin towards the bite layer of said provisional, such that during fitting, resin filler is extruded through the slit into a space to provide contact between adjacent temporaries, said plurality of temporaries integral with one another along a distal medial axis, said coupling means being embedded in said resin filler and extending along said distal medial axis, and wherein said temporary has an incompletely polymerized layer integral with an inner surface of the provisional, such that after polymerization of the temporary bridge, the provisional is bound to the resin filler.

16. A semi-permanent crown for use with a permanent luting cement for protecting a tooth stub comprised of a provisional and a resin filler, said resin filler being unpolymerized and filling a void between the provisional and the tooth stub, said provisional having a bite layer, a pair of opposing neighbour walls, a lingual wall and a buccal wall, said lingual and buccal walls in opposition, said bite layer integral with the neighbour, lingual and buccal walls to define a cavity to accept the tooth stub and resin filler, said bite layer having at least one aperture, said neighbour, buccal and lingual walls having a gingival margin distal to the bite layer, and said neighbour walls being invaginated to define a slit extending from the gingival margin towards the bite layer of said provisional, such that during fitting, resin filler is extruded through the slit into a space between the provisional and an adjacent structure to provide contact with the adjacent structure, wherein the provisional has an incompletely polymerized layer integral with an inner surface of the provisional, such that after polymerization of the resin in situ, the provisional is bound to the resin filler.

\* \* \* \* \*

UNITED STATES PATENT AND TRADEMARK OFFICE
CERTIFICATE OF CORRECTION

PATENT NO. : 6,884,073 B2
DATED : April 26, 2005
INVENTOR(S) : Richard H. Chillibeck It is certified that error appears in the above-identified patent and that said Letters Patent is hereby corrected as shown below:

Column 11,
Line 19, replace "incisal and lingual nianes" with -- incisal and lingual planes --.

Signed and Sealed this

Sixteenth Day of August, 2005

JON W. DUDAS
*Director of the United States Patent and Trademark Office*